United States Patent [19]
Rault et al.

[11] Patent Number: 5,153,190
[45] Date of Patent: Oct. 6, 1992

[54] PYRROLO [1,2A] THIENO [3,2-F] [1,4] DIAZEPINES

[75] Inventors: Sylvain Rault, Moult; Michel Boulouard, Caen; Marie P. Foloppe, Vimoutiers; Max Robba, Paris; Béatrice Guardiola; Michelle Devissague, both of Neuilly sur Seine, all of France

[73] Assignee: Adir et Compagnie, Courbevoie, France

[21] Appl. No.: 665,807

[22] Filed: Mar. 7, 1991

[30] Foreign Application Priority Data

Mar. 8, 1990 [FR] France .................... 90 02934

[51] Int. Cl.⁵ .................... C07D 495/14; A61K 31/55
[52] U.S. Cl. .................... 514/220; 540/560
[58] Field of Search .................... 540/560; 514/220

[56] References Cited

FOREIGN PATENT DOCUMENTS 52-100496 8/1977 Japan .

OTHER PUBLICATIONS

Pyrrolothienopyrazine: Synthése de la pyrrolo [1,2-a]-thieno [3,2-3]pyrazine et de la pyrrolo[1,2]thieno [2,3--e]pyrazine, S. Rault, et al. Journal of Hetrocyclic Chemistry (1983) vol. 20, pp. 17–21.
2-amino thiophene aus methylenaktiven Nitrilen, carbonyl verbindungen und schwefel, K. Gewald, et al., Chem Ber (1966) 99, pp. 94–101.
2-amino thiophene aus a-oxo-mercaptanen und methylenaktiven Nitrilen K. Gewald, Angew. Chem. Ber (1965) 98, pp. 3571–3577.
Aur Reaktion von a-oxo mercaptanen mit Nitrilen Angew Chem. (1961) 73, pp. 114, Gewald.
C. R. Aead. Se. Paris, t. 285(Oct. 31, 1977), vol. C, pp. 381–383, S. Rault, et al.
C. R. Aead. Se Paris, t. 287 (Sep. 11, 1978), vol. C, pp. 117–120, S. Rault, et al.

Primary Examiner—Mukund J. Shah
Assistant Examiner—Philip I. Datlow
Attorney, Agent, or Firm—Gordon W. Hueschen

[57] ABSTRACT

The invention relates to pyrrolo [1,2-a] thieno [3,2-f][1,4]diazepine compounds of the formula (I)

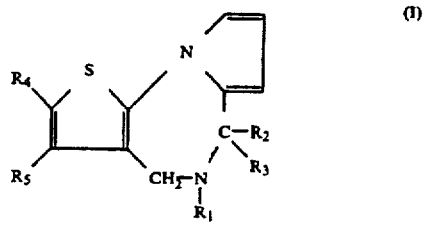

in which: $R_1$ is hydrogen; alkyl optionally substituted with alkoxy, hydroxy, cycloalkyl, or phenyl; or alkyl- or arylsulfonyl; $R_2$ is hydrogen, phenyl, or phenylalkyl; alkyl optionally substituted with hydroxyl, alkoxy, oxo, cycloalkyl or phenyl; or optionally substituted amino; $R_3$ represents hydrogen or alkyl, and $R_4$ and $R_5$ independently represent: hydrogen, alkyl optionally substituted with alkoxy, cycloalkyl, or phenyl; or phenyl; their isomers, diastereoisomers and enantiomers as well as their addition salts with pharmaceutically-acceptable acids. The compounds are useful for treating cerebral ischemia, hypertriglyceridemia, hypercholesterolemia, hyperlipidemia, and hyperglycemia and are obtained in a few steps from the corresponding substituted 2-(1-pyrrolyl)thiophenes

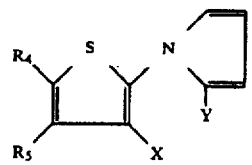

Y—CHO or H; X CN, CONH₂, CH₂NHCOR₂, or CH₂NH₂.

16 Claims, No Drawings

PYRROLO [1,2A] THIENO [3,2-F] [1,4] DIAZEPINES

The present invention relates to novel pyrrolo[1,2-a]thieno[3,2-f][1,4]diazepines, to their process of preparation and to the pharmaceutical compositions containing them.

Some arylthienopyrrolodiazepines are already known for their action on the central nervous system (Japanese Patent 77 100-496).

A few 6-aryl-5,6-dihydro-4H-pyrrolo[1,2-a]thieno[3,2-f][1,4]diazepines are also known, the synthesis of which has been published, without a pharmacological activity being described (S. Rault, Compte Rendus Hebd. des séances de l'Académie des sciences, series C, Vol. 285 No. 11 31 Oct. 1977 Paris pages 381-383).

The pyrrolo[1,2-a]thieno[3,2-f][1,4]diazepines of the Applicant are products endowed with exceptional antihypoxic properties which are very advantageous in the treatment of cerebral aging and stroke.

The aging brain draws continually on its metabolic reserves to maintain its basal metabolism in a viable condition, any additional function demand resulting in an insufficiency of response. The compounds of the Applicant provide a solution to these problems by permitting an increase in the effective consumption of oxygen when there is increased metabolic demand without enhancing it excessively in the basal state. Their antihypermetabolic properties also make them valuable in the treatment of stroke.

The compounds of the Applicant are also extremely advantageous on account of their metabolic effects, since they possess substantial hypocholesterolemic, hypotriglyceridemic and hypoglycemic properties.

Finally, they possess, in greater or lesser degree according to the structure, antihypertensive, anxiolytic and PAF (Platelet Antagonist Factor)-antagonist properties.

More specifically, the invention relates to the pyrrolo[1,2-a]thieno[3,2-f][1,4]diazepines of general formula (I):

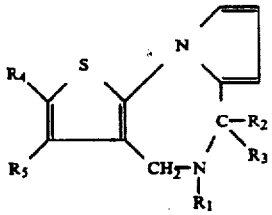

in which $R_1$ represents a hydrogen atom, a lower alkyl group having 1 to 6 carbon atoms, branched or otherwise, optionally substituted with hydroxyl, alkoxy, cycloalkyl or aryl groups, an alkylsulfonyl group or an arylsulfonyl group optionally substituted on the aromatic ring with one or more lower alkyl groups or halogens, $R_4$ and $R_5$ each represent, independently of one another, a hydrogen atom, a lower alkyl group having 1 to 6 carbon atoms, branched or otherwise, optionally substituted with hydroxyl, alkoxy, cycloalkyl or substituted or unsubstituted aryl groups, or an optionally substituted aryl or aralkyl group (the term substituted associated with the expressions aryl or aralkyl means that the aromatic rings may be substituted with one or more alkyl, nitro, alkoxy, trifluoromethyl or halogen groups), $R_2$ and $R_3$ each represent, independently of one another, a hydrogen atom, an optionally substituted aryl or aralkyl group, a lower alkyl group having 1 to 6 carbon atoms, branched or otherwise, optionally substituted with one or more hydroxyl, alkoxy, oxo, cycloalkyl or substituted or unsubstituted aryl groups, or a group —NR'R" for which R' and R" each represent, independently of one another, a hydrogen atom, a group —CO—R''' (R''' represents either an optionally substituted phenyl, or an indolyl, or an optionally substituted anilino group) or a lower alkyl group, or, together with the nitrogen atom to which they are attached, form a mono- or bicyclic heterocyclic system containing or otherwise another hetero atom and optionally substituted with a lower alkyl group or an optionally substituted aryl or aralkyl group (the term substituted for the expressions aryl, phenyl, anilino and aralkyl means that the aromatic rings may be substituted with one or more alkyl, nitro, alkoxy, trifluoromethyl or halogen groups), with the proviso that, when $R_1=R_4=R_5=H$ and one of the two substituents $R_2$ or $R_3$ is a hydrogen atom, then the other substituent can represent neither a hydrogen atom nor a methoxy group nor an optionally substituted aryl group, their isomers, diastereoisomers and enantiomers, their addition salts with a pharmaceutically acceptable inorganic or organic acid.

The invention also encompasses the processes for obtaining the compounds of general formula (I). The optimum processes for obtaining these compounds vary according to the nature of the substituents $R_1$, $R_2$, $R_3$, $R_4$ and $R_5$, and are distinguished by the fact that:

either the starting material is a derivative of general formula (II):

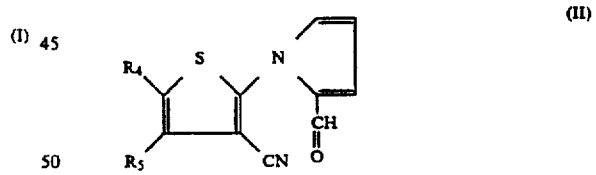

in which $R_4$ and $R_5$ have the same meaning as in the compound of general formula (I), which is reacted in a mixture of aqueous sodium hydroxide solution, ethanol and hydrogen peroxide with a methyl ketone of general formula (III):

in which $R_6$ is a cycloalkyl group or a lower alkyl group having 1 to 6 carbon atoms, branched or otherwise, optionally substituted with alkoxy, cycloalkyl or aryl groups, so as to obtain the 5,6-dihydro-4-oxo-4H -pyrrolo[1,2-a]thieno[3,2-f][1,4]diazepine of general formula (IV):

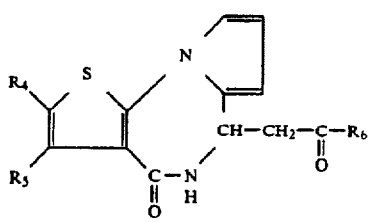
(IV)

in which $R_6$ has the same meaning as in the general formula (III) and $R_4$ and $R_5$ the same meaning as in the compound of general formula (I), which is reduced in an aprotic medium with a mixed metal hydride so as to obtain the 5,6-dihydro-4H-pyrrolo[1,2-a]thieno[3,2-f][1,4]diazepine of general formula (V):

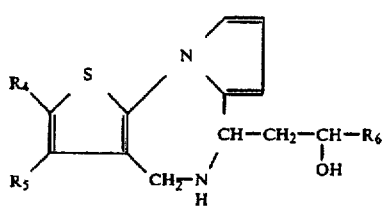
(V)

in which $R_4$, $R_5$ and $R_6$ have the same meaning as in the formula (III), which may be treated in ethereal solution with gaseous hydrochloric acid to obtain the 5,6-dihydro-4H,5H+-pyrrolo[1,2-a]thieno[3,2-f][1,4]diazepinium chloride of general formula (VI):

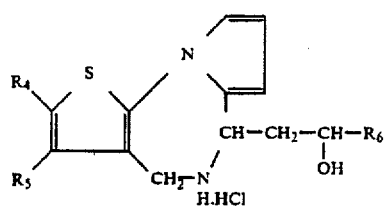
(VI)

in which $R_4$, $R_5$ and $R_6$ have the same meaning as in the formula (III), or the starting material is the compound of general formula (VII):

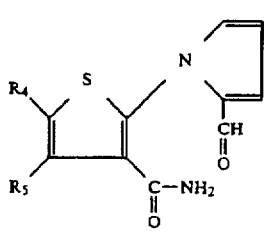
(VII)

in which $R_4$ and $R_5$ have the same meaning as in the compound of general formula (I), which is reacted in suspension in water with a tertiary amine so as to obtain the compound of general formula (VIII):

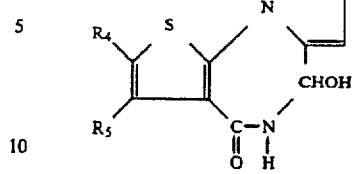
(VIII)

in which $R_4$ and $R_5$ have the same meaning as in the compound of general formula (I), which is reduced in an aprotic medium with a mixed metal hydride so as to obtain the compound of general formula (IX):

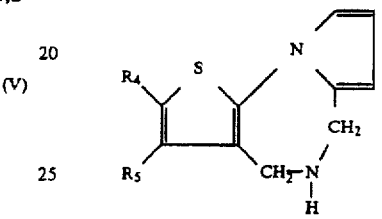
(IX)

in which $R_4$ and $R_5$ have the same meaning as in the compound of general formula (I), which is reacted in the presence of an amine with a halogenated derivative of general formula (X):

$$R_1Cl \qquad (X)$$

in which $R_1$ has the same meaning as in the compound of general formula (I), so as to obtain the compound of general formula (XI):

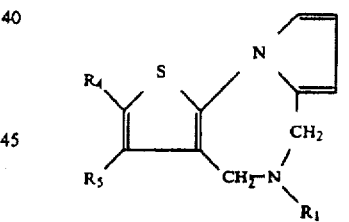
(XI)

in which $R_1$, $R_4$ and $R_5$ have the same meaning as in the compound of general formula (I), or the starting material is the compound of general formula (XII):

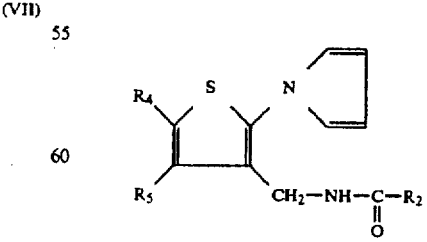
(XII)

in which $R_2$, $R_4$ and $R_5$ have the same meaning as in the compound of general formula (I), which is cyclized with phosphorus oxychloride so as to obtain the compound of general formula (XIII):

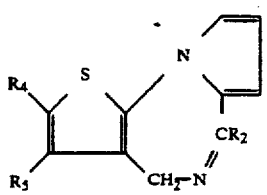
(XIII)

in which $R_2$, $R_4$ and $R_5$ have the same meaning as in the compound of general formula (I), which is reduced in an aprotic medium with a mixed metal hydride so as to obtain the 5,6-dihydro-4H-pyrrolo[1,2-a]thieno[3,2-f][1,4]diazepine of general formula (XIV):

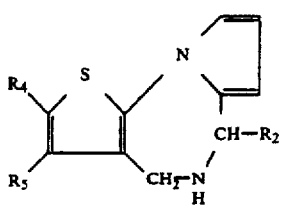
(XIV)

in which $R_2$, $R_4$ and $R_5$ have the same meaning as in the compound of general formula (I), which may be treated in ethereal solution with gaseous hydrochloric acid to obtain the 5,6-dihydro-4H,5H+-pyrrolo[1,2-a]thieno[3,2-f][1,4]diazepinium chloride of general formula (XV):

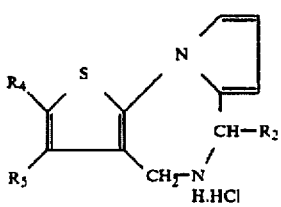
(XV)

in which $R_2$, $R_4$ and $R_5$ have the same meaning as in the compound of general formula (I), or the starting material is the compound of general formula (XVI):

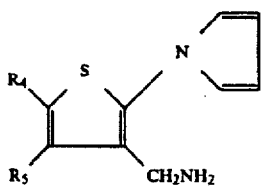
(XVI)

in which $R_4$ and $R_5$ have the same meaning as in the compound of general formula (I), which is reacted in alcohol under reflux with an aldehyde of general formula (XVII):

(XVII)

in which $R_2$ has the same meaning as in the compound of general formula (I), so as to obtain the compound of general formula (XVIII):

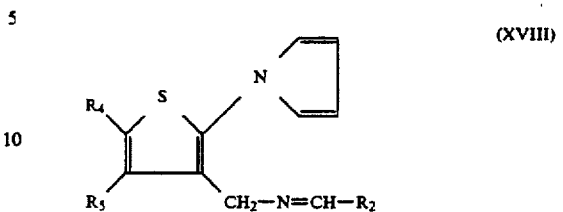
(XVIII)

in which $R_2$, $R_4$ and $R_5$ have the same meaning as in the compound of general formula (I), which is treated in ethereal solution with gaseous hydrochloric acid so as to obtain the 5,6-dihydro-4H,5H+-pyrrolo[1,2-a]thieno[3,2-f][1,4]diazepinium chloride of general formula (XV), in which $R_2$, $R_4$ and $R_5$ have the same meaning as in the compound of general formula (I), or the starting material is the compound of general formula (XIX):

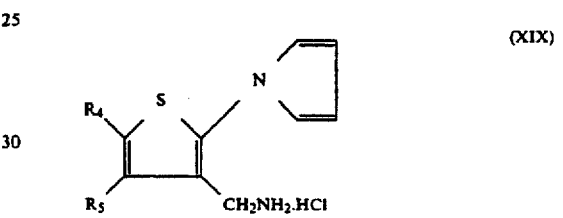
(XIX)

in which $R_4$ and $R_5$ have the same meaning as in the compound of general formula (I), which is reacted under reflux in alcohol and in the presence of concentrated hydrochloric acid with a ketone of general formula (XX):

(XX)

in which $R_2$ and $R_3$ have the same meaning as in the compound of general formula (I), so as to obtain the 5,6-dihydro-4H,5H+-pyrrolo[1,2-a]thieno[3,2-f][1,4]diazepinium chloride of general formula (XXI):

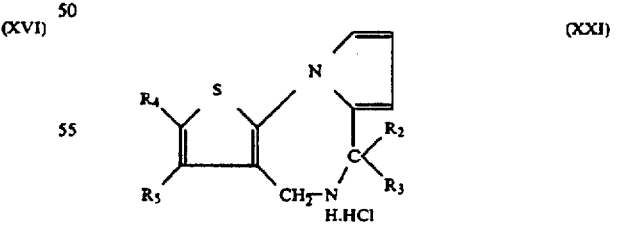
(XXI)

in which $R_2$, $R_3$, $R_4$ and $R_5$ have the same meaning as in the compound of general formula (I), or the starting material is the compound of general formula (XIX), in which $R_4$ and $R_5$ have the same meaning as in the compound of general formula (I), which is reacted in an alcoholic medium with ethyl 2-ethoxy-2-hydroxyacetate so as to obtain the compound of general formula (XXII):

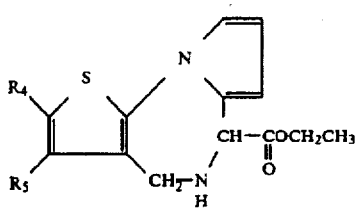
(XXII)

in which $R_4$ and $R_5$ have the same meaning as in the compound of general formula (I), which is reduced in alcoholic solution with a mixed metal hydride so as to obtain the 6-hydroxymethyl-5,6-dihydro-4H-pyrrolo[1,2-a]thieno[3,2-f][1,4]diazepine of general formula (XXIII):

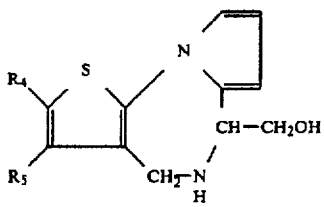
(XXIII)

in which $R_4$ and $R_5$ have the same meaning as in the compound of general formula (I), or the starting material is the compound of general formula (VIII), in which $R_4$ and $R_5$ have the same meaning as in the compound of general formula (I), which is reacted under reflux of acetonitrile with an amine of general formula (XXIV):

HNR'R''      (XXIV)

in which R' and R'' have the same meaning as in the compound of general formula (I), so as to obtain the compound of general formula (XXV):

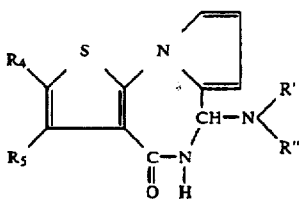
(XXV)

in which $R_4$, $R_5$, R' and R'' have the same meaning as in the compound of general formula (I), which is reduced in an aprotic medium with a mixed metal hydrode so as to obtain the compound of general formula (XXVI):

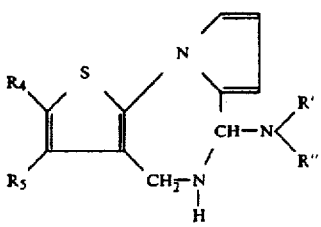
(XXVI)

in which $R_4$, $R_5$, R' and R'' have the same meaning as in the compound of general formula (I).

The compounds of general formula V, VI, IX, XI, XIV, XV, XXI, XXII, XXIII and XXVI form part of the invention and represent the compounds of general formula (I).

The pyrrolo[1,2-a]thieno[3,2-f][1,4]diazepines of general formula (I), as well as their addition salts with a pharmaceutically acceptable inorganic or organic acid, are active principles possessing exceptional pharmacological and therapeutic properties.

These compounds possess strong antihypoxic properties which make them valuable in the treatment, inter alia, of cerebral aging, stroke and, more generally, ischemic syndromes of any localization. They are capable in mice of prolonging survival of the cerebral tissue during acute hypoxia.

These compounds also exhibit very advantageous metabolic properties, since they are strongly hypocholesterolemic, hypotriglyceridemic, hypolipidemic and hypoglycemic, leading to a very large number of potential therapeutic applications (obesity, atheroma, hyperlipidemia, hypercholesterolemia, etc.).

Finally, these compounds possess, and in greater or lesser degree according to their structure, antihypertensive, anxiolytic and PAF-antagonist properties.

The pyrrolo[1,2-]thieno[3,2-f][1,4]diazepines of general formula (I), as well as their addition salts with a pharmaceutically acceptable inorganic or organic acid such as, for example, hydrochloric, methanesulfonic, citric and maleic acids, may be made into pharmaceutical preparations according to generally known processes, such as, for example, into tablets, hard gelatin capsules, dragees, solutions for oral administration, injectable solutions, suspensions for oral administration, emulsions and suppositories.

Apart from inert, non-toxic and pharmaceutically acceptable excipients such as, for example, distilled water, glucose, lactose, starch, talc, vegetable oils, ethylene glycol, and the like, these preparations can also contain preservatives, stabilizers, wetting agents, emulsifiers, and the like.

The compositions thereby obtained are generally presented in the form of measured doses and can contain, depending on the conditions treated and the patient's age and sex, from 0.1 to 500 mg of active principle. They can, depending on the case, be administered orally, rectally or parenterally at dose of 0.1 to 500 mg from one to several times a day.

The examples which follow illustrate the invention and in no way limit the latter.

The characteristics of the $^1H$ NMR spectrometry are collated in Tables I.

EXAMPLE 1

6-(2-Hydroxypentyl)-5,6-dihydro-4H, 5H+-pyrrolo[1,2-a]thieno[3,2-f][1,4]diazepinium chloride Stage I: 6-(2-Oxo-1-pentyl)-5,6-dihydro-4-oxo-4H-pyrrolo[1,2-]thieno[3,2-f][1,4]diazepine.

A solution of 12 g (0.059 mole) of 2-(2-formyl-1-pyrrolyl)-3-cyanothiophene in a mixture of 200 cm³ of 2-pentanone, 200 cm³ of ethanol, 200 cm³ of 5N sodium hydroxide and 15 cm³ of 33% hydrogen peroxide is heated to reflux for one hour. The ethanol and 2-pentanone are then removed under reduced pressure and the remainder of the reaction medium is poured into 200 cm³ of cold water. The precipitate formed is isolated by filtration, washed with water, dried and then recrystallized in an ether/acetone mixture.

11,5 g (68%) of 6-(2-oxo-1-pentyl)-5,6-dihydro-4-oxo-4H-pyrrolo[1,2-a]thieno[3,2-f][1,4]diazepine are thereby obtained in the form of yellow crystals.

M.P. 186° C. (ether/acetone)
Microanalysis: $C_{15}H_{16}N_2O_2S$ M = 288.36;
Calculated: C 62.49% H 5.59% N 9.72% S 11.10%;
Found: C 62.48% H 5.50% N 9.72% S 11.23%;

| IR spectrum (KBr) | 3275 and 3170 cm⁻¹ | NH bands |
| --- | --- | --- |
| | 3050, 2950, 2920, and 2870 cm⁻¹ | CH bands |
| | 1705 cm⁻¹ | C=O (ketone) band |
| | 1640 cm⁻¹ | C=O (lactam) band |

Stage II: 6-(2-Hydroxypentyl)-5,6-dihydro-4H, 5H+-pyrrolo[1,2-a]thieno[3,2-f][1,4]diazepinium chloride.

A solution of 2.6 g (0.009 mole) of 6-(2-oxo -1-pentyl)-5,6-dihydro-4-oxo-4H-pyrrolo[1,2-a]thieno[3,2-f][1,4]diazepine in 550 cm³ of dichloromethane is added dropwise to a suspension of 1.50 g (0.04 mole) of lithium aluminum hydride in 20 cm³ of ethyl ether. The reaction mixture is stirred at room temperature for 30 minutes and then heated to reflux for 6 hours. After cooling, the solution obtained is cast on to 250 g of ice. The emulsion formed is filtered, the organic phase separated after settling has taken place and the aqueous phase extracted with 200 cm³ of methylene chloride. The organic phases are combined, dried over calcium chloride, purified on animal charcoal and then concentrated under reduced pressure. The residual oil is taken into solution in 300 cm³ of ethyl ether and the hydrochloride precipitated by bubbling gaseous hydrochloric acid through the solution. The precipitate obtained is filtered off, washed with ether and recrystallized in isopropanol.

1,4 g (50%) of 6-(2-hydroxypentyl)-5,6-dihydro-4H,5H+-pyrrolo[1,2-a]thieno[3,2-f][1,4]diazepinium chloride are thereby obtained in the form of gray crystals.

M.p. 214° C. (isopropanol)
Microanalysis: $C_{15}H_{21}N_2OSCl$ M = 312.86;
Calculated: C 57.59% H 6.76% S 10.25% Cl 11.33%;
Found: C 57.80% H 7.09% S 9.59% Cl 10.69%;

| IR spectrum (KBr) | 3350 cm⁻¹ | OH band |
| --- | --- | --- |
| | 3310 cm⁻¹ | CH band |
| | 2960 to 2550 cm⁻¹ | $NH_2^+Cl^-$ broad band main bands |
| | 1565, 1430, 1330, 1130, 1100, 960 and 735 cm⁻¹ | |

EXAMPLE 2

6-(2-Cyclopropyl-2-hydroxyethyl)-5,6-dihydro -4H,5H+-pyrrolo[1,2-a]thieno[3,2-f][1,4]diazepine chloride Stage I: 6-(2-Cyclopropyl-2-oxoethyl)-5,6-dihydro-4-oxo-4H-pyrrolo[1,2-a]thieno[3,2-f][1,4]diazepine.

Same working protocol as for Stage I of Example 1, starting with 6 g (0.029 mole) of 2-(2-formyl-1-pyrrolyl)-3-cyanothiophene and 50 cm³ of cyclopropyl methyl ketone.

4,80 g (57%) of 6-(2-cyclopropyl-2-oxoethyl)-5,6-dihydro-4-oxo-4H-pyrrolo[1,2-a]thieno[3,2-f][1,4]diazepine are thereby obtained in the form of white crystals.

M.p. 200° C. (ethyl ether/acetone)
Microanalysis: $C_{15}H_{14}N_2O_2S$ M = 286.35;
Calculated: C 62.91% H 4.92% N 9.78% S 11.19%;
Found: C 62.87% H 4.93% N 9.81% S 11.05%;

| IR spectrum (KBr) | 3270 and 3180 cm⁻¹ | NH bands |
| --- | --- | --- |
| | 3120, 3090, 3050 and 2890 cm⁻¹ | CH bands |
| | 1685 and 1640 cm⁻¹ | C=O bands |

Stage II: 6-(2-Cyclopropyl-2-hydroxyethyl)-5,6-dihydro-4H,5H+-pyrrolo[1,2-a]thieno[3,2-f][1,4]diazepine in 400 cm³ of dichloromethane and 0.7 g (0.017 mole) of lithium aluminum hydrode in 20 cm³ of ethyl ether.

0,7 g (54%) of 6-(2-cyclopropyl-2-hydroxyethyl)-5,6-dihydro-4H,5H+-pyrrolo[1,2-a]thieno[3,2-f][1,4]diazepinium chloride is thereby obtained in the form of white crystals.

M.p. 236° C. (isopropanol)
Microanalysis: $C_{15}H_{19}N_2OSCl$ M = 310.84;
Calculated: C 57.96% H 6.16% N 0.01% Cl 11.41%;
Found: C 57.74% H 6.07% N 8.80% Cl 11.62%;

| IR spectrum (KBr) | 3350 cm⁻¹ | OH band |
| --- | --- | --- |
| | 3310, 2980 cm⁻¹ | CH band |
| | 2970 to 2540 cm⁻¹ | $NH_2^+Cl^-$ broad band main bands |
| | 1565, 1480, 1330, 1100, 1025, 960, 825, 760 and 735 cm⁻¹ | |

EXAMPLE 3

6-(2-Hydroxy-3-methylbutyl)-5,6-dihydro -4H,5H+-pyrrolo[1,2-a]thieno[3,2-f][1,4]diazepinium chloride Stage I: 6-(3-Methyl-2-oxo-1-butyl) -5,6-dihydro-4-oxo-4H-pyrrolo[1,2-a]thieno[3,2-f][1,4]diazepine.

Same working protocol as for Stage I of Example 1, starting with 12 g (0.059 mole) of 2-(2-formyl -1-pyrrolyl)-3-cyanothiophene and 100 cm³ of isopropyl methyl ketone.

11.1 g (65%) of 6-(3-methyl-2-oxo-1-butyl)-5,6-dihydro-4-oxo-4H -pyrrolo[1,2-a]thieno[3,2-f][1,4]diazepine are thereby obtained in the form of yellow crystals.

M.p. 160° C. (ethanol)
Microanalysis: $C_{15}H_{16}N_2O_2S$ M = 288.35;
Calculated: C 62.49% H 5.59% N 9.72% S 11.10%;
Found: C 62.50% H 5.80% N 9.69% S 11.07%;

| IR spectrum (KBr) | 3280 and 3175 cm⁻¹ | NH bands |
| --- | --- | --- |
| | 3060, 2960, 2930 and 2880 cm⁻¹ | CH bands |
| | 1710 and 1650 cm⁻¹ | C=O bands |

Stage II: 6-(2-Hydroxy-3-methylbutyl)-5,6-dihydro-4H,5H+-pyrrolo[1,2-a]thieno[3,2-f][1,4]diazepinium chloride.

Same working protocol as for Stage II of Example 1, starting with 1.4 g (0.0049 mole) of 6-(3-methyl-2-oxobutyl)-5,6-dihydro-4-oxo -4H-pyrrolo[1,2-a]thieno[3,2-f][1,4]diazepine in 400 cm³ of dichloromethane and 0.76 g (0.020 mole) of lithium aluminum hydride in 20 cm³ of ethyl ether.

0.8 g (52%) of 6-(2-hydroxy-3-methylbutyl)-5,6-dihydro-4H,5H+-pyrrolo[1,2-a]thieno[3,2- f][1,4]diazepinium chloride is thereby obtained in the form of a white powder.

M.p. 236° C. (isopropanol)

Microanalysis: $C_{15}H_{21}N_2OSCl$ M=312.86;

Calculated: C 57.96% H 6.76% S 10.25% Cl 11.33%; found: C 57.50% H 6.88% S 9.67% Cl 11.02%;

| IR spectrum (KBr) | 3380 cm$^{-1}$ | OH band |
|---|---|---|
| | 3110 cm$^{-1}$ | CH band |
| | 2960 to 2560 cm$^{-1}$ | $NH_2^+Cl^-$ broad band |
| | 1570, 1480, 1330, 1260, 1090, and 715 cm$^{-1}$ | main bands. |

EXAMPLE 4

6-(2-Phenyl-2-hydroxyethyl)-5,6-dihydro-4H,5H+-pyrrolo[1,2-a]thieno[3,2-f][1,4]diazepinium chloride Stage I: 6-Phenacyl-5,6-dihydro-4-oxo-4H-pyrrolo[1,2-a]thieno[3,2-f][1,4]diazepine.

Same working protocol as for Stage I of Example 1, starting with 1 g (0.0049 mole) of 2-(2-formyl-1-pyrrolyl)-3-cyanothiophene, 20 cm$^3$ of acetophenone, 100 cm$^3$ of 6N sodium hydroxide, 50 cm$^3$ of ethanol and 5 cm$^3$ of 33% hydrogen peroxide. After removal of the ethanol under reduced pressure, the reaction medium is poured into 100 cm$^3$ of water. The oily precipitate which is composed of acetophenone and the oxodiazepine is extracted with ethyl ether. The ether phase is washed with water, dried over magnesium sulfate and concentrated under reduced pressure. The acetophenone is removed by washing the residue with a petroleum ether/ethyl ether (50:50) mixture. The insoluble solid remaining is filtered off, dried and recrystallized in ethanol.

0.7 g (44%) of 6-phenacyl-5,6-dihydro-4-oxo-4H-pyrrolo[1,2-a]thieno[3,2-f][1,4]diazepine is thereby obtained in the form of white crystals.

M.p. 205° C. (ethanol)

Microanalysis: $C_{18}H_{14}N_2O_2S$ M=322.37;

Calculated: C 67.07% H 4.38% N 8.69% S 9.93%; Found: C 66.83% H 4.63% N 8.80% S 9.68%.

| IR spectrum (KBr) | 3320 and 3260 cm$^{-1}$ | NH bands |
|---|---|---|
| | 3090, 3060, and 2920 cm$^{-1}$ | CH bands |
| | 1675 and 1640 cm$^{-1}$ | C=O bands |
| | 1595, 1535, 1480, 1430, 1325, 1215, 775 and 685 cm$^{-1}$ | main bands. |

Stage II: 6-(2-phenyl-2-hydroxyethyl)-5,6-dihydro-4H,5H+-pyrrolo[1,2-a]thieno[3,2-f][1,4]diazepinium chloride.

Same working protocol as for Stage II of Example 1, starting with 1.6 g (0.005 mole) of 6-phenacyl-5,6-dihydro-4-oxopyrrolo[1,2-a]thieno[3,2-f][1,4]diazepine in 450 cm$^3$ of dichloromethane and 0.76 g (0.02 mole) of lithium aluminum hydride in 20 cm$^3$ of ethyl ether.

0.9 g (52%) of 6-(2-phenyl-2-hydroxyethyl)-5,6-dihydro-4H,5H+-pyrrolo[1,2-a]thieno[3,2-f][1,4]diazepinium chloride is thereby obtained in the form of white crystals.

M.p. 186° C. (isopropanol)

Microanalysis: $C_{18}H_{19}N_2OSCl$ M=346.87.

Calculated: C 62.33% H 5.52% S 9.24% Cl 10.22%. Found: C 61.96% H 5.77% S 8.89% Cl 9.89%.

| IR spectrum (KBr) | 3340 cm$^{-1}$ | OH bands |
|---|---|---|
| | 3110 cm$^{-1}$ | CH band |
| | 2970 to 2540 cm$^{-1}$ | $NH_2^+Cl^-$ broad band |
| | 1565, 1330, 1100, 1070, 960 865, 735 and 705 cm$^{-1}$ | main bands. |

EXAMPLE 5

6-(2-Hydroxypropyl)-5,6-dihydro-4H, 5H+-pyrrolo[1,2-a]thieno[3,2-f][1,4]diazepinium chloride Stage I: 6-(2-Oxopropyl) and 5,6-dihydro-4-oxo-4H-pyrrolo[1,2-a]thieno[3,2-f][1,4]diazepine.

Same working protocol as for Stage I of Example 1, starting with acetone.

Stage II: 6-(2-Hydroxypropyl)-5,6-dihydro-4H, 5H+-pyrrolo[1,2-a]thieno[3,2-f][1,4]diazepinium chloride.

Same working protocol as for Stage II of Example 1, starting with 5 g (0.019 mole) of 6-(2-oxopropyl)-5,6-dihydro-4-oxo-4H-pyrrolo[1,2-a]thieno[3,2-f][1,4]diazepine in 500 cm$^3$ of dichloromethane and 2.9 g (0.076 mole) of lithium aluminum hydride in 20 cm$^3$ of ethyl ether.

2,2 g (41%) of 6-(2-hydroxypropyl)-5,6-dihydro-4H,5H+-pyrrolo[1,2-a]thieno[3,2-f][1,4]diazepinium chloride are thereby obtained in the form of beige crystals.

M.p. 226° C. (isopropanol)

Microanalysis: $C_{13}H_{17}N_2OSCl$ M=284.8.

Calculated: C 54.82% H 6.02% S 11.26% Cl 12.45%. Found: C 54.98% H 6.04% S 11.09% Cl 12.67%.

| IR spectrum (KBr) | 3390 cm$^{-1}$ | OH band |
|---|---|---|
| | 3110 cm$^{-1}$ | CH band |
| | 2960 to 2580 cm$^{-1}$ | $NH_2^+Cl^-$ broad band |
| | 1570, 1480, 1330, 1180, 1100, 730 and 700 cm$^{-1}$ | main bands. |

EXAMPLE 6

6-(2-Hydroxypropyl)-5,6-dihydro-4H-pyrrolo[1,2-a]thieno[3,2-f][1,4]diazepine

A solution of 1 g (0.0035 mole) of 6-(2-hyroxypropyl)-5,6-dihydro-4H,5H+-pyrrolo[1,2-a]thieno[3,2-f][1,4]diazepinium chloride in 50 cm$^3$ of water is alkalinized to pH 14 using sodium hydroxide pellets. The emulsion obtained is extracted with 3 times 50 cm$^3$ of ethyl ether. The organic phases are separated after settling has taken place, combined, dried over magnesium sulfate and concentrated under reduced pressure until a crude product is obtained, which product is recrystallized in ethyl ether.

0.70 g (80%) of 6-(2-hydroxypropyl) -5,6-dihydro-4H-pyrrolo[1,2-a]thieno[3,2-f][1,4]diazepine is thereby obtained in the form of white crystals.

M.p. 130° C. (Et$_2$O)

Microanalysis: $C_{13}H_{16}N_2OS$ M=248.34.

Calculated: C 62.87% H 6.49% N 11.28% S 12.91%. Found: C 62.74% H 6.55% N 11.21% S 12.75%.

| IR spectrum (KBr) | 3240 cm$^{-1}$ | NH band |
|---|---|---|
| | 3080, 2920, and 2830 cm$^{-1}$ | CH bands |
| | 1580, 1480, 1310, 1135 and | main bands |

-continued

| | |
|---|---|
| 705 cm$^{-1}$ | |

EXAMPLE 7

6-(2-Phenyl-2-hydroxyethyl)-5,6-dihydro-4H-pyrrolo[1,2-a]thieno[3,2-f][1,4]diazepine Same working protocol as for Example 6, starting with 1 g (0.0029 mole) of 6-(2-phenyl-2-hydroxyethyl)-5,6-dihydro-4H,5H+-pyrrolo[1,2-a]thieno[3,2-f][1,4]diazepinium chloride.

0.72 g (80%) of 6-(2-phenyl-2-hydroxyethyl)-5,6-dihydro-4H-pyrrolo[1,2-a]thieno[3,2-f][1,4]diazepine is thereby obtained in the form of white crystals.

M.p. 190° C. (Et$_2$O)
Microanalysis: C$_{18}$H$_{16}$N$_2$O$_2$S M=324.40.
Calculated: C 66.65% H 4.97% N 8.64% S 9.88%.
Found: C 66.56% H 4.89% N 8.52% S 9.68%.

| IR spectrum (KBr) | 3300 cm$^{-1}$ | NH band |
|---|---|---|
| | 3100 and 2920 cm$^{-1}$ | CH bands |
| | 1580, 1480, 1330, 1095 and 705 cm$^{-1}$ | main bands |

EXAMPLE 8

5-para-Tolylsulfonyl-5,6-dihydro-4H-pyrrolo[1,2-a]thieno[3,2-f][1,4]diazepine Stage I: 6-Hydroxy-5,6-dihydro-4-oxo-4H-pyrrolo[1,2-a]thieno[3,2-f][1,4]diazepine.

0.5 cm$^3$ of triethylamine is added to a suspension of 2-(2-formyl-1-pyrrolyl)-3-carboxamidothiophene in 60 cm$^3$ of water. The reaction medium is stirred for 12 hours at ambient temperature. The product gradually passes into solution and then reprecipitates. The precipitate obtained is isolated by filtration, washed with water, isolated and then recrystallized in water.

1.35 g (68% of 6-hydroxy-5,6-dihydro-4-oxo-4H-pyrrolo[1,2-a]thieno[3,2-f][1,4]diazepine are thereby obtained in the form of beige crystals.

M.p. 166° C.
Microanalysis: C$_{16}$H$_8$N$_2$O$_2$S M=220.45.
Calculated: C 54.53% H 3.66% N 12.71% S 14.56%.
Found: C 54.36% H 3.69% N 12.58% S 14.39%.

| IR spectrum (KBr) | 3340 cm$^{-1}$ | OH band |
|---|---|---|
| | 3220 cm$^{-1}$ | NH band |
| | 3210 and 3110 cm$^{-1}$ | CH bands |
| | 1610 cm$^{-1}$ | C=O band |
| | 1500, 1450, 1320, 1205, 1005, 830 and 720 cm$^{-1}$ | main bands |

Stage II: 5,6-Dihydro-4H-pyrrolo[1,2-a]thieno[3,2-f][1,4]diazepine.

A solution of 3 g (0.014 mole) of 6-hydroxy-5,6-dihydro-4-oxo-4H-pyrrolo[1,2-a]thieno[3,2-f][1,4]diazepine in 300 cm$^3$ of dilchloromethane is added dropwise to a suspension of 2.08 g (0.055 mole) of lithium aluminum hydride in 15 cm$^3$ of ethyl ether. The reaction medium is stirred for 30 minutes at room temperature and then heated to reflux for 6 hours.

After cooling, the solution obtained is cast on to 200 g of ice and the emulsion formed is drained. The organic phase is separated after settling has taken place and the aqueous phase extracted with 200 cm$^3$ of dichloromethane. The organic phases are combined, dried over calcium chloride, purified on animal charcoal and concentrated under reduced pressure. 2.4 g (90%) of 5,6-dihydro-4H-pyrrolo[1,2-a]thieno[3,2-f][1,4]diazepine are thereby obtained in the form of an oil.

Stage III: 5-para-Tolylsulfonyl-5,6-dihydro-4H-pyrrolo[1,2-a]thieno[3,2-f][1,4]diazepine.

An excess of para-toluenesulfonyl chloride is added to a solution of 1 g (0.0053 mole) of 5,6-dihydro-4H-pyrrolo[1,2-a]thieno[3,2-f][1,4]diazepine in 10 cm$^3$ of pyridine, and the reaction mixture is then stirred at room temperature for one hour. The pyridine is removed by distillation under reduced pressure and the oily residue ground in 100 cm$^3$ of water. The emulsion formed is extracted with 3 times 100 cm$^3$ of ethyl ether.

The organic phases are separated after settling has taken place, combined, washed with acidulated water, dried over magnesium sulfate and finally concentrated under reduced pressure.

The solid obtained is then recrystallized in ethyl ether.

0.5 g (27%) of 5-para-tolylsulfonyl-5,6-dihydro-4-pyrrolo[1,2-a]thieno[3,2-f][1,4]diazepine is thereby obtained in the form of beige crystals.

M.p. 173° C. (ethyl ether)
Microanalysis: C$_{17}$H$_{16}$N$_2$O$_2$S M=344.44.
Calculated: C 59.28% H 4.68% N 8.13% S 18.68%.
Found: C 59.15% H 4.74% N 8.06% S 19.40%.

| IR spectrum (KBr) | 3100, 2960, 2820 cm$^{-1}$ | CH bands |
|---|---|---|
| | 1580, 1485, 1350, 1330, 1155, 1080, 905, 805, 710 and 655 cm$^{-1}$ | main bands |

EXAMPLE 9

6,6-Dimethyl-5,6-dihydro-4H,5H+-pyrrolo[1,2-a]thieno[3,2-f][1,4]diazepinium chloride A solution of 2 g (0.0093 mole) of 2-(1-pyrrolyl)-3-(aminomethyl)thiophene hydrochloride in a mixture of 10 cm$^3$ of acetone, 50 cm$^3$ of methanol and 5 cm$^3$ of concentrated hydrochloric acid is heated to reflux for 3 hours. After cooling, the precipitate formed by the addition of petroleum ether is isolated by filtration, washed with ethyl ether and recrystallized in isopropanol.

1.5 g (59%) of 6,6-dimethyl-5,6-dihydro-4H,5H+-pyrrolo[1,2-a]thieno[3,2-f][1,4]diazepinium chloride are thereby obtained.

M.P. 250° C. (isopropanol)
Microanalysis: C$_{12}$H$_{15}$N$_2$SCl M=254.76.
Calculated: C 56.57% H 5.93% Cl 13.91% N 10.94%.
Found: C 56.53% H 6.07% Cl 13.70% N 10.94%.

| IR spectrum (KBr) | 2910, 2660 and 2620 cm$^{-1}$ | NH$_2^+$ bands |
|---|---|---|
| | 1575, 1560, 1480, 1440, 1340, 980, 875 and 745 cm$^{-1}$ | main bands |

EXAMPLE 10

6-Hydroxymethyl-5,6-dihydro-4H-pyrrolo[1,2-a]thieno[3,2-f][1,4]diazepine 0.60 g (0.015 mole) of sodium borohydride is added to a solution of 2 g (0.007 mole) of 6-ethoxycarbonyl-5,6-dihydro-4H-pyrrolo[1,2-a]thieno[3,2-f][1,4]diazepine in 30 cm$^3$ of methanol. The reaction medium is brought to reflux for 2 hours and the methanol is then removed under reduced pressure. The residue is taken up with 100 cm³ of water and the aqueous solution is extracted with ethyl acetate.

The organic phases are decolorized over animal charcoal, dried over magnesium sulfate and concentrated under reduced pressure.

The white precipitate obtained is recrystallized in ethyl ether.

1 g (60%) of 6-hydroxymethyl-5,6-dihydro-4H-pyrrolo[1,2-a]thieno[3,2-f][1,4]diazepine is thereby obtained in the form of white crystals.

M.p. 166° C. (ethyl ether)
Microanalysis: $C_{11}H_{12}N_2OS$ M=220.28.
Calculated: C 59.98% H 5.49% N 12.72% S 14.55%.
Found: C 60.04% H 5.58% N 12.61% S 14.38%.

| IR spectrum (KBr) | 3430 cm⁻¹ | OH band |
| --- | --- | --- |
| | 3260 cm⁻¹ | NH band |
| | 1580, 1480, 1400, 1340, 1320, 1160, 1040, 840 and 720 cm⁻¹ | main bands |

6-Ethoxycarbonyl-5,6-dihydro-4H-pyrrolo[1,2-a]thieno[3,2-f][1,4]diazepine is obtained by condensation of 2-(1-pyrrolyl)-3-(aminomethyl)thiophene with ethyl 2-ethoxy-2-hydroxyacetate in an ethanolic medium.

EXAMPLE 11

6-Cyclopropyl-5,6-dihydro-4H,5H⁺-pyrrolo[1,2-a]thieno[3,2-f][1,4]diazepinium chloride A solution of 2 g (0.008 mole) of 6-cyclopropyl-4H-pyrrolo[1,2-a]thieno[3,2-f][1,4]diazepine in 50 cm³ of anhydrous ethyl ether is added dropwise to a suspension of 0.30 g (0.008 mole) of lithium aluminum hydride in 50 cm³ of anhydrous ethyl ether. The reaction medium is brought to reflux for 4 hours, then cooled and poured slowly into 100 cm³ of water.

The ether phase is separated after settling has taken place, washed with water, dried over magnesium sulfate and concentrated under reduced pressure. 6-Cyclopropyl-5,6-dihydro-4H-pyrrolo[1,2-a]thieno[3,2-f][1,4]diazepine is thereby obtained in the form of an oil.

This oil is taken up in 50 cm³ of ethyl ether and a stream of gaseous hydrochloric acid is bubbled through for 1 minute. The precipitate is isolated by filtration, washed with ethyl ether and then recrystallized in isopropanol.

6-Cyclopropyl-5,6-dihydro-4H,5H⁺-pyrrolo[1,2-a]thieno[3,2-f][1,4]diazepinium chloride is thereby obtained in a 90% yield.

M.p. 250° C. (isopropanol)
Microanalysis: $C_{13}H_{15}N_2SCl$ M=266.78.
Calculated C 58.92% H 5.67%.
Found: C 57.94% H 5.62%.

| IR spectrum (KBr) | 2920, 2780 and 2560 cm⁻¹ | NH₂⁺ bands |
| --- | --- | --- |
| | 3120 cm⁻¹ | CH band |
| | 1570, 1480, 1440, 1340, 1140, 1100, 900 and 880 cm⁻¹ | main bands |

6-cyclopropyl-4H-pyrrolo[1,2-a]thieno[3,2-f][1,4]diazepine is obtained by condensation of cyclopropanecarboxylic acid chloride with 2-(1-pyrrolyl)-3-(aminomethyl) thiophene in pyridine, followed by a cyclization of the amide formed by means of POCL₃.

EXAMPLE 12

6-Methyl-5,6-dihydro-4H,5H⁺-pyrrolo[1,2-a]thieno[3,2-f][1,4]diazepinium chloride Same working protocol as for Example 11, starting with 6-methyl-4H-pyrrolo[1,2-a]thieno[3,2-f][1,4]diazepine. The 6-Methyl-5,6-dihydro-4H-pyrrolo[1,2-a]thieno[3,2-f][1,4]diazepine obtained is purified by distillation under vacuum. The corresponding hydrochloride is prepared in the same manner as in Example 11.

6-Methyl-5,6-dihydro-4H,5H⁺-pyrrolo[1,2-a]thieno[3,2-f][1,4]diazepinium chloride is thereby obtained in a 90% yield.

M.p. 242° C. (isopropanol)
Microanalysis: $C_{11}H_{13}N_2SCl$ M=240.75.
Calculated: C 54.88% H 5.44% Cl 14.73% S 13.32%.
Found: C 55.54% H 5.64% Cl 14.08% S 12.83.

| IR spectrum (KBr) | 2920, 2600 cm⁻¹ | NH₂⁺ bands |
| --- | --- | --- |
| | 1570, 1550, 1480, 1440, 1390, 1330, 1260, 1180, 1100, 1030 and 970 cm⁻¹ | main bands |

6-Methyl-4H-pyrrolo[1,2-a]thieno[3,2-f][1,4]diazepine is obtained by acylation of 2-(2-pyrrolyl)-3-(aminomethyl)thiophene in a mixture of acetic acid and acetic anhydride, followed by a cyclization of the amide formed by means of phosphorus oxychloride.

EXAMPLE 13

6-Ethyl-5,6-dihydro-4H,5H⁺-pyrrolo[1,2-a]thieno[3,2-f][1,4]diazepinium chloride

Same working protocol as for Example 11, starting with 6-ethyl-4H-pyrrolo[1,2-a]thieno[3,2-f][1,4]diazepine. 6-Ethyl-5,6-dihydro-4H, 5H⁺-pyrrolo[1,2-a]thieno[3,2-f][1,4]diazepinium chloride is thereby obtained in a 95% yield.

M.p. 194° C. (isopropanol)
Microanalysis: $C_{12}H_{15}N_2SCl$ M=254.77.
Calculated: C 56.57% H 5.93S 12.58%.
Found: C 56.81% H 5.85% S 12.69%.

| IR spectrum (KBr) | 2920, 2740, 2540 cm⁻¹ | NH₂⁺ bands |
| --- | --- | --- |
| | 1570, 1480, 1380, 1260, 1170, 1100, 900 and 860 cm⁻¹ | main bands |

6-Ethyl-4H-pyrrolo[1,2-a]thieno[3,2-f][1,4]diazepine is obtained by acylation of 2(1-pyrrolyl)-3-(aminomethyl)thiophene in pyridine with propionyl chloride, followed by a cyclization of the amide formed by means of phosphorus oxychloride.

EXAMPLE 14

2,3-Dimethyl-5,6-dihydro-4H,5H⁺-pyrrolo[1,2-a]thieno[3,2-f][1,4]diazepinium chloride Stage I: 4,5-Dimethyl-2-(1-pyrrolyl)-3-cyanothiophene.

A solution of 2 g (0.0145 mole) of 2-amino-3-cyano-4,5-dimethylthiophene and 2 cm³ (0.0160 mole) of 2,5-dimethoxytetrahydrofuran in 25 cm³ of acetic acid is heated to reflux for 30 minutes. The acetic acid is removed under vacuum and the residual brown oil distilled.

2 g (68%) of 4,5-dimethyl-2-(1-pyrrolyl)-3-cyanothiophene are thereby obtained in the form of white crystals.

M.p. 45° C.

Microanalysis: $C_{11}H_{10}N_2S$ M=344.44.
Calculated: C 65.32% H 4.98% N 13.85% S 15.85%.
Found: C 65.15% H 5.08% N 13.63% S 15.63%.

| IR spectrum (KBr) | 3170 and 2920 cm$^{-1}$ | CH bands |
|---|---|---|
| | 2220 cm$^{-1}$ | CN band |
| | 1520, 1425, 1090, 915 and 720 cm$^{-1}$ | main bands |

Stage II: 4,5-Dimethyl-2-(2-formyl-1-pyrrolyl)-3-cyanothiophene.

13 g (0.064 mole) of 4,5-dimethyl-2-(1-pyrrolyl)-3-cyanothiophene, dissolved in 20 cm³ of DMF, are added at room temperature and in a single portion to a complex, prepared beforehand at 0° C., of 7.4 cm³ (0.096 mole) of DMF and 8.8 cm³ (0.096 mole) of phosphorus oxychloride. The reaction and then 1 hour at 100° C. After cooling, the reaction medium is poured on to 300 g of ice, stirred for 20 minutes and then alkanized with 6N sodium hydroxide solution. The precipitate formed is isolated by filtration, washed with water, dried and then recrystallized in ethyl ether.

13.7 g (93%) of 4,5-dimethyl-2-(2-formyl-1-pyrrolyl)-3-cyanothiophene are thereby obtained in the form of white crystals.

M.p. 154° C. (ethyl ether)

Microanalysis: $C_{12}H_{10}N_2OS$ M=230.25.
Calculated: C 62.61% H 4.34% N 12.17% S 13.9%.
Found: C 62.74% H 4.49% N 12.09% S 14.04%.

| IR spectrum (KBr) | 3030, 2840 and 2750 cm$^{-1}$ | CH bands |
|---|---|---|
| | 2220 cm$^{-1}$ | CN band |

Stage III: 4,5-Dimethyl-2-(2-formyl-1-pyrrolyl)-3-thiophenecarboxylic acid.

A solution of 5 g (0.022 mole) of 4,5-dimethyl-2-(2-formyl-1-pyrrolyl)-3-cyanothiophene in 100 cm³ of 6N sodium hydroxide and 120 cm³ of ethanol is heated to reflux for 6 hours. The ethanol is removed under reduced pressure and the aqueous solution diluted with 200 cm³ of water and acidified with 2N hydrochloric acid solution. The precipitate formed is isolated by filtration, washed with water, dried and recrystallized.

3.5 g (64%) of 4,5-dimethyl-2-(2-formyl-1-pyrrolyl)-3-thiophenecarboxylic acid are thereby obtained.

Stage IV: 4,5-Dimethyl-2-(2-formyl-1-pyrrolyl)-3-carboxamidothiophene.

1.2 cm³ (0.008 mole) of triethylamine are added at 0° C. to a suspension of 2 g (0.008 mole) of 4,5-dimethyl-2-(2-formyl-1-pyrrolyl)-3-thiophenecarboxylic acid in 200 cm³ of ethyl ether. After stirring for 20 minutes, 0.8 cm³ (0.008 mole) of ethyl chloroformate is added to the suspension maintained at 0° C. The reaction mixture is stirred for 20 minutes and the precipitate of triethylammonium chloride formed is then removed by filtration. Ammonia is bubbled into the solution maintained at 0° C., and the precipitate which forms instantaneously is isolated by filtration. The precipitate is washed with ether, dried and recrystallized.

1.19 g (60%) of 4,5-dimethyl-2-(2-formyl-1-pyrrolyl)-3-carboxamidothiophene are thereby obtained.

Stage V: 2,3-Dimethyl-6-hydroxy-4-oxo-5,6-dihydro-4H-pyrrolo[1,2-a]thieno[3,2-f][1,4]diazepine.

2 g (0.008 mole) of 4,5-dimethyl-2-(2-formyl-1-pyrrolyl)-3-carboxamidothiophene are suspended in 20 cm³ of water and then stirred at room temperature. The precipitate obtained is isolated by filtration, washed with water, dried and then recrystallized.

1.29 g (65%) of 2,3-dimethyl-6-hydroxy-5,6-dihydro-4-oxo-4H-pyrrolo[1,2-a]thieno[3,2-f][1,4]diazepine are thereby obtained.

Stage VI: 2,3-Dimethyl-5,6-dihydro-4H, 5H+-pyrrolo[1,2-a]thieno[3,2-f][1,4]diazepinium chloride.

Same working protocol as for Stage II of Example 8, starting with 5 g (0.02 mole) of 2,3-dimethyl-6-hydroxy-4-oxo-5,6-dihydro-4H -pyrrolo[1,2-a]thieno[3,2-f][1,4]diazepine.

The oil obtained is taken up in 300 cm³ of ethyl ether and a stream of gaseous hydrochloric acid is then bubbled through the mixture. The precipitate obtained is isolated by filtration, washed with ethyl ether and then recrystallized.

2.60 g (51%) of 2,3-dimethyl-5,6-dihydro -4H,5H+-pyrrolo[1,2-a]thieno[3,2-f][1,4]diazepinium chloride are thereby obtained.

M.p. above 260° C.

TABLE Ia (The chemical shifts are in ppm)

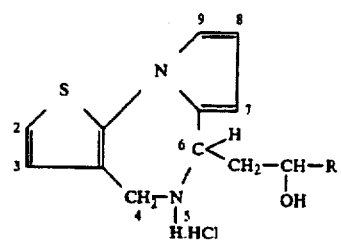

| Ex | R | H$_2$ | H$_3$ | H$_7$ | H$_8$ | H$_9$ | NH$_2^\oplus$ 5 | CH$_2$ 4 | H$_6$ | Other protons | |
|---|---|---|---|---|---|---|---|---|---|---|---|
| 1 | CH$_2$CH$_2$CH$_3$ | 7.45 | 7.12 | 6.44 | 6.36 | 7.26 | 9.97 | 4.16 | 4.21 | OH | 4.38 |
| | | | | | | | | | | CH$_2$ | 3.54 |
| | | | | | | | | | | CH | 3.70 |
| | | | | | | | | | | 2CH$_2$ | 1.36 |
| | | | | | | | | | | CH$_3$ | 0.86 |

TABLE Ia-continued (The chemical shifts are in ppm)

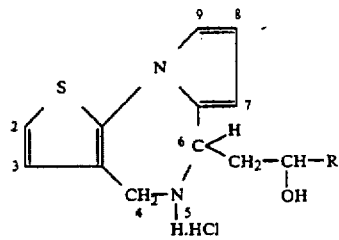

| Ex | R | $H_2$ | $H_3$ | $H_7$ | $H_8$ | $H_9$ | $NH_2^{\oplus}$ 5 | $CH_2$ 4 | $H_6$ | Other protons | |
|---|---|---|---|---|---|---|---|---|---|---|---|
| 2 | CH₂–CH–CH₂ (cyclopropyl) | 7.46 | 7.13 | 6.43 | 6.35 | 7.27 | 9.93 | 4.17 | 4.25 | OH<br>CH<br>CH<br>$CH_2$<br>$2CH_2$ | 4.90<br>3.68<br>0.84<br>3.54<br>0.38 and 0.20 |
| 3 | CH(CH₃)₂ | 7.41 | 7.06 | 6.40 | 6.33 | 7.23 | 9.77 | 4.18 | 4.26 | OH<br>$CH_2$<br>CH<br>CH<br>$2CH_2$ | 4.84<br>3.60<br>3.72<br>1.58<br>0.84 |
| 4 | $C_6H_5$ | 7.48 | 7.14 | 6.61 | 6.41 | 7.30 | 9.86 | 4.28 | 4.54 | OH<br>$CH_2$<br>CH<br>$C_6H_5$ | 5.66<br>3.60<br>3.72<br>7.38; 7.36 and 7.32 |
| 5 | $CH_3$ | 7.45 | 7.12 | 6.49 | 6.35 | 7.27 | 10 | 3.96 | 4.25 | OH<br>CH<br>$CH_2$<br>$CH_3$ | 4.84<br>3.61<br>3.37<br>1.07 |

TABLE Ib (The chemical shifts are in ppm)

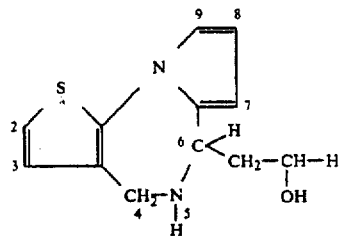

| Ex | R | $H_2$ | $H_3$ | $H_7$ | $H_8$ | $H_9$ | NH 5 | $H_6$ | $CH_2$ 4 | Other protons | |
|---|---|---|---|---|---|---|---|---|---|---|---|
| 6 | $CH_3$ | 6.90 | 6.70 | 6.06 | 6.19 | 7.00 | 6.95 | 4.11 | 4.24 | CH<br>$CH_3$<br>$CH_2$ | 4.02<br>1.25<br>1.87–2.04 |
| 7 | $C_6H_5$ | 6.91 | 6.62 | 6.06 | 6.15 | 6.96 | 6.95 | 4.35 | 4.33 | CH<br>$CH_2$<br>$C_6H_5$ | 3.74<br>2.49<br>7.37 |

TABLE Ic (The chemical shifts are in ppm)

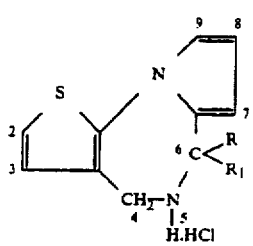

| Ex | $H_3$ | $H_7$ | $H_8$ | $H_9$ | $CH_2$ 4 | $CH_2$ 6 | Other protons |
|---|---|---|---|---|---|---|---|
| 8 | 6.87 | 6.16 | 6.12 | 6.87 | 4.42 | 3.37 | $CH_3$ 2.33 $C_6H_4$ 7.52 and 7.26 |

TABLE Id (The chemical shifts are in ppm)

| Ex | R | $R_1$ | $H_2$ | $H_3$ | $H_7$ | $H_8$ | $H_9$ | $CH_2$ 4 | Other protons |
|---|---|---|---|---|---|---|---|---|---|
| 9 | $CH_3$ | $CH_3$ | 7.30 | 6.93 | 6.20 | 6.30 | 7.10 | 4.1 | $CH_3$ 1.6 $NH_2^\oplus$ 10.3 |
| 11 | H | $CH\begin{smallmatrix}CH_2\\ \\CH_2\end{smallmatrix}$ | 7.38 | 7.06 | 6.35 | 6.60 | 7.23 | 4.25 / 3.70 | $H_6$ 2.5 cyclopropyl 1.55; 0.7; 0.32 $NH_2^\oplus$ 10.09 |
| 12 | H | $CH_3$ | 7.42 | 7.10 | 6.34 | 6.44 | 7.25 | 4.28 / 3.63 | $H_6$ 4.08 $CH_3$ 1.66 $NH_2^\oplus$ 10.28 |
| 13 | H | $C_2H_5$ | 7.41 | 7.09 | 6.34 | 6.44 | 7.24 | 4.22 / 3.61 | $H_6$ 3.90 $CH_2(C_2H_5)$ to 2.05 $CH_3(C_2H_5)$ to 0.9 |

TABLE Ie (The chemical shifts are in ppm)

| Ex | R | $R_1$ | $H_2$ | $H_3$ | $H_7$ | $H_8$ | $H_9$ | $CH_2$ | Other protons |
|---|---|---|---|---|---|---|---|---|---|
| 10 | H | $CH_2OH$ | 7.12 | 6.78 | 6.04 | 6.11 | 7.01 | 4.00 | $CH_2$ 3.65 OH 4.71 |

TABLE Ie-continued (The chemical shifts are in ppm)

| Ex | R | $R_1$ | $H_2$ | $H_3$ | $H_7$ | $H_8$ | $H_9$ | $CH_2$ | Other protons |
|---|---|---|---|---|---|---|---|---|---|
| | | | | | | | | | $H_6$ 3.8 |

TABLE If (The chemical shifts are in ppm)

| Ex | $H_7$ | $H_8$ | $H_9$ | Other protons |
|---|---|---|---|---|
| 14 | 6.39 | 6.27 | 7.18 | $CH_2$: 3.95 (s) $CH_2$: 4.10 (s) $CH_3$: 2.06 (s) $CH_2$: 2.25 (s) $NH_2^\oplus$: 10.05 |

EXAMPLE 15

Tablet containing 3 mg of 2,3-dimethyl-5,6-dihydro-4H,5H+-pyrrolo[1,2-a]thieno[3,2-f][1,4]diazepinium chloride.

| | |
|---|---|
| 2,3-Dimethyl-5,6-dihydro-4H,5H+-pyrrolo[1,2-a]thieno[3,2-f][1,4]diazepinium chloride | 3 g |
| Wheat starch | 110 g |
| Cornstarch | 85 g |
| Magnesium stearate | 15 g |
| Talc | 20 g | per 1000 tablets containing 3 mg of active principle.

EXAMPLE 16

Pharmacological Study

Demonstration of the antihypoxic properties a) Principle

During aging, the fall in intrinsic cerebral reserves results in an inability to respond to any fresh metabolic demand.

During stroke, selective neuronal vulnerability appears in the cells which have the greatest metabolic demand.

The common point between these pathologies is the deficit in oxygen utilisation which, more often than not, leads the metabolism to veer towards the anaerobic state.

Stresses of this kind may be reproduced experimentally and acutely by hypoxia in order to investigate novel cerebroprotective compounds.

In effect, the analogy between hypoxia and the cerebral disorders linked to aging or to circulatory insufficiency are expressed, in particular, by:

a fall in the energy reserves, a lower resistance to stress, a fall in the oxygen-dependent synthesis of neurotransmitters, a drop in mnestic capacity.

The compounds of the present invention were hence tested for their capacity to prolong survival of the cerebral tissue in mice.

b) Methodology

Male CD1 mice (Charles River) are subjected to an acute hypoxia of the hypobaric type 30 minutes after receiving the test compound intraperitoneally. For this purpose, they are placed in a chamber in which the barometric pressure may be lowered rapidly to a value of 160 mbar.

The renewal of air effected during the test makes it possible to produce a hypoxia and not an asphyxia or an anoxia which could require a protection of vascular origin.

Brain death is obtained in approximately 15 seconds after production of the hypoxic pressure.

The mean survival time of a treated batch is compared with that of a control batch receiving only the injection solvent.

c) Results

The compounds of the invention do not bring about a neuro-behavioral effect of the sedation type, in contrast to diazepam. They significantly counteract cerebral hypoxia.

Acute hypoxia: Percentage increase in cerebral survival time.

| Example | mg/kg IP | | | |
|---|---|---|---|---|
| | 3 | 10 | 30 | 100 |
| 2 | +12 | +17 | +22 | +94 |
| 3 | +9 | +11 | +19 | +82 |
| 5 | +11 | +15 | +27 | +125 |
| 14 | +35 | +54 | +128 | +250 |

We claim:

1. A pyrrolo[1,2-a]thieno[3,2-f][1,4]diazepine selected from those of the formula (I):

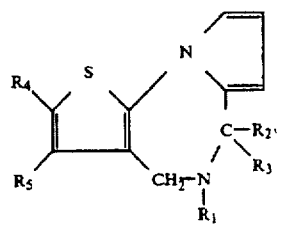

in which
$R_1$ represents hydrogen, lower alkyl having 1 to 6 carbon atoms, inclusive, branched or otherwise, optionally substituted with hydroxyl, $C_1-C_6$ alkoxy, $C_3-C_7$ cycloalkyl or phenyl; $C_1-C_3$ alkylsulfonyl or phenylsulfonyl optionally substituted on the aromatic ring with one or more $C_1-C_3$ lower alkyl or halogen, $R_4$ and $R_5$ each represent, independently of one another, hydrogen, lower alkyl having 1 to 6 carbon atoms, inclusive, branched or otherwise, optionally substituted with hydroxyl, $C_1-C_6$ alkoxy, $C_3-C_7$ cycloalkyl or substituted or unsubstituted phenyl, or phenyl or phenyl $C_1-C_3$-alkyl optionally substituted with one or more $C_1-C_3$ alkyl, nitro, $C_1-C_3$ alkoxy, trifluoromethyl or halogen, $R_2$ represents hydrogen, optionally substituted phenyl or phenyl $C_1-C_3$-alkyl, lower alkyl having 1 to 6 carbon atoms, inclusive, branched or otherwise, optionally substituted with one or more hydroxyl, $C_1-C_6$ alkoxy, oxo, $C_3-C_7$ cycloalkyl or substituted or unsubstituted phenyl, or a group —NR'R" in which R' and R" each represent, independently of one another, hydrogen, —CO—R'''
wherein R''' represents an optionally-substituted phenyl, or an indolyl, or an optionally-substituted anili-1- or -2-yl group, or a $C_1-C_6$ lower alkyl group or, together with the nitrogen atom to which they are attached, R' and R" form a monocyclic heterocyclic system optionally-substituted with $C_1-C_6$ lower alkyl or an optionally-substituted phenyl or phenyl $C_1-C_3$-alkoxy group, the term "substituted" associated with the expressions phenyl, anili-1- or -2-yl, and phenyl $C_1-C_3$-alkyl, where not otherwise specified, meaning that the aromatic rings may be substituted with one or more $C_1-C_3$ alkyl, nitro, $C_1-C_3$ alkoxy, trifluoromethyl or halogen groups or atoms, and $R_3$ = hydrogen or $C_1-C_3$ alkyl;

with the proviso that, when three of $R_1$, $R_4$, and $R_5$ are H or unsubstituted alkyl, then $R_2$ can represent neither a hydrogen atom, a methyl (when $R_3$ equals H), a phenyl, or substituted phenyl group, its isomers, diastereoisomers and enantiomers, and its addition salts with a pharmaceutically-acceptable inorganic or organic acid.

2. A compound as claimed in claim 1 for which $R_4$ and $R_5$ represent either a hydrogen atom or a lower alkyl group having 1 to 6 carbon atoms, as well as its isomers and their addition salts with a pharmaceutically-acceptable acid.

3. A compound as claimed in claim 1 which is selected from 6-(2-hydroxypentyl)-5,6-dihydro-4H-pyrrolo[1,2-a]thieno[3,2-f][1,4]diazepine of the following formula, as well as its isomers, and their addition salts with a pharmaceutically-acceptable acid

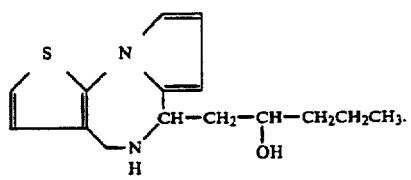

4. A compound as claimed in claim 1 which is selected from 6-(2-cyclopropyl-2-hydroxyethyl)-5,6-dihydro-4H-pyrrolo[1,2-a]thieno[3,2-f][1,4]diazepine of the following formula, as well as its isomers and their addition salts with a pharmaceutically-acceptable acid

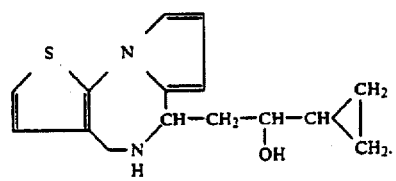

5. A compound as claimed in claim 1 which is selected from 6-(2-hydroxy-3-methylbutyl)-5,6-dihydro-4H-pyrrolo[1,2-a]thieno[3,2-f][1,4]diazepine of the following formula, as well as its isomers, and their addition salts with a pharmaceutically-acceptable acid

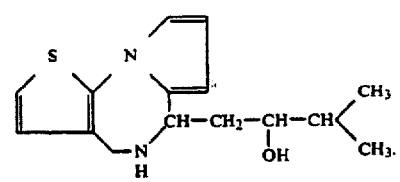

6. A compound as claimed in claim 1 which is selected from 6-(2-phenyl-2-hydroxyethyl)-5,6-dihydro-4H-pyrrolo[1,2-a]thieno[3,2-f][1,4]diazepine of the following formula as well as its isomers, and their addition salts with a pharmaceutically-acceptable acid

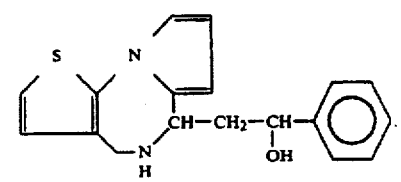

7. A compound as claimed in claim 1 which is selected from 6-(2-hydroxypropyl)-5,6-dihydro-4H-pyrrolo[1,2-a]thieno[3,2-f][1,4]diazepine of the following formula, as well as its isomers, and their addition salts with a pharmaceutically-acceptable acid

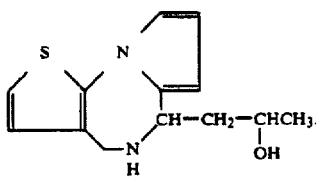

8. A compound as claimed in claim 1 which is 5-para-tolylsulfonyl-5,6-dihydro-4H-pyrrolo[1,2-a]thieno[3,2-f][1,4]diazepine of the following formula

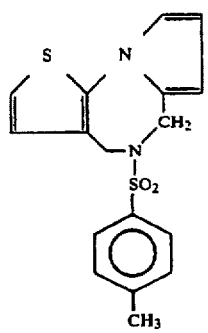

9. A compound as claimed in claim 1 which is 6,6-dimethyl-5,6-dihydro-4H-pyrrolo[1,2-a]thieno[3,2-f][1,4]diazepine of the following formula, as well as its addition salts with a pharmaceutically-acceptable acid

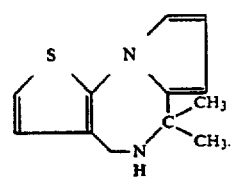

10. A compound as claimed in claim 1 which is selected from 6-(hydroxymethyl)-5,6-dihydro-4H-pyrrolo[1,2-a]thieno[3,2-f][1,4]diazepine of the following formula, as well as its isomers, and their addition salts with a pharmaceutically-acceptable acid

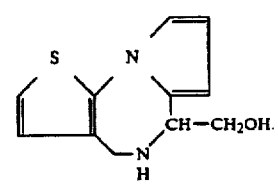

11. A compound as claimed in claim 1 which is selected from 6-cyclopropyl-5,6-dihydro-4H-pyrrolo[1,2-a]thieno[3,2-f][1,4]diazepine of the following formula, as well as its isomers, and their addition salts with a pharmaceutically-acceptable acid

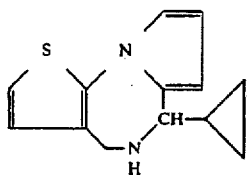

12. A method as claimed in claim 1 wherein the compound is selected from 6-methyl-5,6-dihydro-4H-pyrrolo[1,2-a]thieno[3,2-f][1,4]diazepine of the following formula, as well as its isomers, and their addition salts with a pharmaceutically-acceptable acid

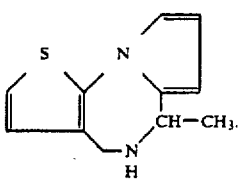

13. A compound as claimed in claim 1 which is selected from 6-ethyl-5,6-dihydro-4H-pyrrolo[1,2-a]thieno[3,2-f][1,4]diazepine of the following formula, as well as its isomers, and their addition salts with a pharmaceutically-acceptable acid

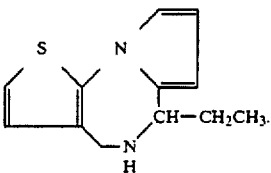

14. A compound which is selected from the group consisting of 2,3-dimethyl-5,6-dihydro-4H-pyrrolo[1,2-a]thieno[3,2-f][1,4]diazepine of the following formula and its addition salts with a pharmaceutically-acceptable acid

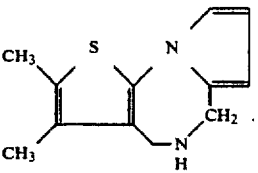

15. A pharmaceutical composition useful for combating ischemia or cerebral hypoxia, aging and a metabolic disease selected from hypercholesterolemia, hyperlipidemia, hypertriglyceridemia, and hyperglycemia, containing as active principle an effective amount of a compound which is a pyrrolo[1,2-a]thieno[3,2-f][1,4]diazepine selected from those of the formula (I):

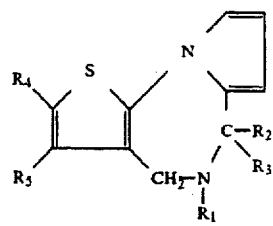

(I)

in which $R_1$ represents hydrogen, lower alkyl having 1 to 6 carbon atoms, branched or otherwise, optionally substituted with hydroxyl, $C_1$–$C_6$ alkoxy, $C_3$–$C_7$ cycloalkyl or phenyl; $C_1$–$C_3$ alkylsulfonyl or phenylsulfonyl optionally substituted on the aromatic ring with one or more $C_1$–$C_3$ lower alkyl or halogen, $R_4$ and $R_5$ each represent, independently of one another, hydrogen, lower alkyl having 1 to 6 carbon atoms, branched or otherwise, optionally substituted with hydroxyl, $C_1$–$C_6$ alkoxy, $C_3$–$C_7$ cycloalkyl or substituted or unsubstituted phenyl, or phenyl or phenyl $C_1$–$C_3$-alkyl optionally substituted with one or more $C_1$–$C_3$ alkyl, nitro, $C_1$–$C_3$ alkoxy, trifluoromethyl or halogen, $R_2$ represents hydrogen, optionally substituted phenyl or phenyl $C_1$–$C_3$-alkyl, lower alkyl having 1 to 6 carbon atoms, branched or otherwise, optionally substituted with one or more hydroxyl, $C_1$–$C_6$ alkoxy, oxo, $C_3$–$C_7$ cycloalkyl or substituted or unsubstituted phenyl, or a group —NR'R" in which R' and R" each represent, independently of one another, hydrogen, —CO—R''' wherein R''' represents an optionally-substituted phenyl, or an indolyl, or an optionally-substituted anili-1- or -2-yl group, or a $C_1$–$C_6$ lower alkyl group or, together with the nitrogen atom to which they are attached, R' and R" form a monocyclic heterocyclic system optionally-substituted with $C_1$–$C_6$ lower alkyl or an optionally-substituted phenyl or phenyl $C_1$–$C_3$-alkoxy group, the term "substituted" associated with the expressions phenyl, anili-1- or -2-yl, and phenyl $C_1$–$C_3$-alkyl, where not otherwise specified, meaning that the aromatic rings may be substituted with one or more $C_1$–$C_3$ alkyl, nitro, $C_1$–$C_3$ alkoxy, trifluoromethyl or halogen groups or atoms, and $R_3$ = hydrogen or $C_1$–$C_3$ alkyl;

with the proviso that, when $R_1$=$R_4$=$R_5$=H and one of the two substituents $R_2$ or $R_3$ is a hydrogen atom, the other substituent can represent neither a hydrogen atom or an optionally-substituted aryl group, its isomers, diastereoisomers and enantiomers, and its addition salts with a pharmaceutically-acceptable inorganic or organic acid, in combination with a pharmaceutically-acceptable excipient or vehicle.

16. A method for treating a living mammal afflicted with ischemia or cerebral hypoxia, comprising the step of administering to the said living animal an amount of a compound which is a pyrrolo[1,2-a]thieno[3,2-f][1,4]diazepine selected from those of the formula (I):

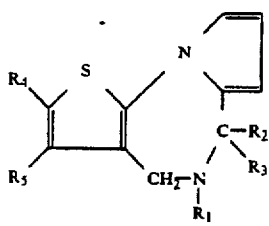

in which
- $R_1$ represents hydrogen, lower alkyl having 1 to 6 carbon atoms, branched or otherwise, optionally substituted with hydroxyl, $C_1$-$C_6$ alkoxy, $C_3$-$C_7$ cycloalkyl or phenyl; $C_1$-$C_3$ alkylsulfonyl or phenylsulfonyl optionally substituted on the aromatic ring with one or more $C_1$-$C_3$ lower alkyl or halogen,
- $R_4$ and $R_5$ each represent, independently of one another, hydrogen, lower alkyl having 1 to 6 carbon atoms, branched or otherwise, optionally substituted with hydroxyl, $C_1$-$C_6$ alkoxy, $C_3$-$C_7$ cycloalkyl or substituted or unsubstituted phenyl, or phenyl or phenyl $C_1$-$C_3$-alkyl optionally substituted with one or more $C_1$-$C_3$ alkyl, nitro, $C_1$-$C_3$ alkoxy, trifluoromethyl or halogen,
- $R_2$ represents hydrogen, optionally substituted phenyl or phenyl $C_1$-$C_3$-alkyl, lower alkyl having 1 to 6 carbon atoms, branched or otherwise, optionally substituted with one or more hydroxyl, $C_1$-$C_6$ alkoxy, oxo, $C_3$-$C_7$ cycloalkyl or substituted or unsubstituted phenyl, or a group —NR'R" in which R' and R" each represent, independently of one another, hydrogen, —CO—R''' wherein R''' represents an optionally-substituted phenyl, or an indolyl, or an optionally-substituted anili-1- or -2-yl group, or a $C_1$-$C_6$ lower alkyl group or, together with the nitrogen atom to which they are attached, R' and R" form a monocyclic heterocyclic system optionally-substituted with $C_1$-$C_6$ lower alkyl or an optionally-substituted phenyl or phenyl $C_1$-$C_3$-alkoxy group,
- the term "substituted" associated with the expressions phenyl, anili-1- or -2-yl, and phenyl $C_1$-$C_3$-alkyl, where not otherwise specified, meaning that the aromatic rings may be substituted with one or more $C_1$-$C_3$ alkyl, nitro, $C_1$-$C_3$ alkoxy, trifluoromethyl or halogen groups or atoms,
- and $R_3$=hydrogen or $C_1$-$C_3$ alkyl;
- with the proviso that, when $R_1=R_4=R_5=H$ and one of the two substituents $R_2$ or $R_3$ is a hydrogen atom, the other substituent can represent neither a hydrogen atom or an optionally-substituted aryl group,
- its isomers, diastereoisomers and enantiomers, and
- its addition salts with a pharmaceutically-acceptable inorganic or organic acid,
- which is effective for alleviation of the said condition.

* * * * *

UNITED STATES PATENT AND TRADEMARK OFFICE
CERTIFICATE OF CORRECTION

PATENT NO. : 5,153,190

DATED : Oct. 6, 1992

Page 1 of 2

INVENTOR(S) : Sylvain Rault, Michel Boulouard, Marie P. Foloppe, Max Robba, Beatrice Guardiola, Michelle Devissaguet It is certified that error appears in the above-identified patent and that said Letters Patent is hereby corrected as shown below:

Title Page, [75] Inventors, 5th line; Devissague" should read --Devissaguet--.

Title Page [56], References Cited, OTHER PUBLICATIONS, line 2; "[1,2]" should read -- [1,2-a]--.

Title Page [56] OTHER PUBLICATIONS, line 11; "Aur" should read --Zur--.

Title Page [57] ABSTRACT, last two lines; "Y—CHO or H; X CN," should read -- Y = -CHO or H; X = CN, --.

Column 1, approximately line 25; "function" should read --functional --.

Column 7, approximately line 55; "hydrode" should read -- hydride --.

Column 8, line 27; "[1,2-]" should read -- [1,2-a] --.

Column 9, approximately line 58; "diazepine" should read --diazepinium--.

Column 10, line 12, 13; "diazepine in 400" should read --diazepinium chloride.

Same working protocol as for Stage II of Example 1, starting with 1.2 g (0.0042 mole) of 6- (2-cyclopropy-2-oxoethyl)-5,6-dihydro-4-oxo-4H-pyrrolo [1,2-a]thieno [3,2-f] [1,4]diazepine in 400--.

Column 10, line 21; "0.01%" should read -- 9.01% --.

Column 11, line 6; "found" should read -- Found --.

Column 12, approximately line 67; "3080, 2920, and" should read -- 3080, 2960, 2920, and --.

Column 13, line 50; "3210" should read -- 3120 --.

Column 14, line 5; "5,5" should read -- 5,6 --.

Column 14, line 21; "dihydro-4-" should read --dihydro-4H- --.

Column 15, line 53; "(isopropanol" should read --(isopropanol)--.

Column 16, line 18; "12.83. should read -- 12.83%. --

Column 16, line 27; "2-(2-pyrrolyl)" should read --2-(1-pyrrolyl)--.

Column 17, approximately line 21; "The reaction and then" should read -- The reaction medium is stirred for 20 minutes at room temperature and then--.

Column 21, Table Id, Example 12, last column, second line; "1.66" should read -- 1.65 --.

Column 24, line 67; "or substituted" should read -- or a substituted --.

UNITED STATES PATENT AND TRADEMARK OFFICE
CERTIFICATE OF CORRECTION

PATENT NO. : 5,153,190
DATED : October 6, 1992
INVENTOR(S) : Sylvain Rault, et al.

It is certified that error appears in the above-identified that said Letters Patent is hereby corrected as shown below:

Column 27, line 2, "1" should read --16--.
Column 27, approximately lines 61-63, delete line 2 beginning "aging" through line 4 ending "hyperglycemia,".

Column 28, line 20 "halogen," should read --halogens, --.
Column 29, line 20, "halogen," should read--halogens,--.
Column 30, line 14, "alkoxy" should read--alkyl--.

This Certificate supersedes Certificate of Correction issued October 26, 1993.

Signed and Sealed this

Ninth Day of August, 1994

BRUCE LEHMAN

Attest:

Attesting Officer

Commissioner of Patents and Trademarks